(12) United States Patent
Speck

(10) Patent No.: US 9,629,942 B2
(45) Date of Patent: Apr. 25, 2017

(54) LIMUS-COATED MEDICAL DEVICES

(75) Inventor: Ulrich Speck, Berlin (DE)

(73) Assignees: Innora GmbH, Berlin (DE); Cordin Corporation, Warren, NJ (US)

( * ) Notice: Subject to any disclaimer, the term of this patent is extended or adjusted under 35 U.S.C. 154(b) by 905 days.

(21) Appl. No.: 13/641,490

(22) PCT Filed: Apr. 19, 2011

(86) PCT No.: PCT/EP2011/056248
§ 371 (c)(1),
(2), (4) Date: Oct. 16, 2012

(87) PCT Pub. No.: WO2011/131678
PCT Pub. Date: Oct. 27, 2011

(65) Prior Publication Data
US 2013/0041315 A1 Feb. 14, 2013

(30) Foreign Application Priority Data

Apr. 19, 2010 (EP) ..................................... 10160352

(51) Int. Cl.
*A61F 2/00* (2006.01)
*A61L 29/16* (2006.01)
*A61L 31/16* (2006.01)

(52) U.S. Cl.
CPC ............... *A61L 29/16* (2013.01); *A61L 31/16* (2013.01)

(58) Field of Classification Search
None
See application file for complete search history.

(56) References Cited

U.S. PATENT DOCUMENTS 9,011,896 B2 * 4/2015 Speck et al. .................. 424/423
2010/0209472 A1 * 8/2010 Wang ........................... 424/423

* cited by examiner

*Primary Examiner* — Hasan Ahmed
(74) *Attorney, Agent, or Firm* — Wood, Phillips, Katz, Clark & Mortimer

(57) ABSTRACT

The present invention is related to a medical device carrying at least on a portion of its surface a Limus drug or Limus drug preparation and butylated hydroxytoluene at a ratio of 3-100% by weight of butylated hydroxytoluene in relation to 100% by weight of the Limus drug.

9 Claims, No Drawings

LIMUS-COATED MEDICAL DEVICES

FIELD OF THE INVENTION

Limus-drugs are a family of structurally related compounds which bind to the mammalian Target of Rapamycin. Limus drugs are known to inhibit vascular renarrowing due to neointimal proliferation following balloon angioplasty and stent implantation if coated on a stent and slowly released during the period when healing of the vessel takes place, i.e. during days and weeks after stent implantation. The invention relates to the transfer of a Limus-drug loosely adhering to the surface of a medical device to a site inside the body, usually in a diseased blood vessel. The most frequent application is local drug therapy during percutaneous transluminal angioplasty (PTA) or percutaneous transluminal coronary angioplasty (PTCA). These interventions are performed to restore blood flow in stenotic or occluded blood vessels, usually in arteries. A catheter is introduced into a major artery. At the distal end the catheter carries a cylindrical balloon in folded state with very small diameter. In this state the balloon can enter or pass the stenotic or occluded segment of the blood vessel. Once positioned in the narrowed segment, the balloon is inflated with high pressure to enlarge the lumen of the blood vessel to its original diameter. Simultaneously, a drug may be transferred to the vessel wall to prevent early renarrowing due to hyperproliferation of the injured vessel wall.

BACKGROUND

Medical devices may contain drugs either to improve the tolerance, efficacy or in vivo life-time of the device or the device serves as carrier for the drug. In any case the dose density (e.g. mg drug/mg device or mg drug/mm$^2$ device surface), chemical stability, adherence, release rate, and total amount released are important and frequently critical features of the drug formulation. These properties are the more critical the more the requirements during production and application of the device vary or may even be contradictory. Drug-coated angioplasty catheters are typical examples: the drug coating must adhere firmly to tolerate mechanical stress during production including folding of balloons, crimping of stents, packaging, transportation to customers, and during final application, which involves passage through a narrow hemostatic valve, an introductory sheath or guiding catheter and a variable distance through possibly tortuous and narrow blood vessels. When the balloon is inflated the drug should be released within a minute or less as rapidly and as completely as possible. The problem was demonstrated by Cremers et al. (Cremers B, Biedermann M, Mahnkopf D, Böhm M, Scheller B. Comparison of two different paclitaxel-coated balloon catheters in the porcine coronary restenosis model. Clin Res Cardiol 2009; 98:325-330) who retrieved as much as 50% of the dose from balloons after expansion for one minute in coronary arteries of pigs, whereas other catheters coated with the same drug and dose but in a different formulation released more than 95%. Almost perfect results (i.e., loss of only 10% of dose and residual drug on the balloon after expansion in an artery of about 10%) were achieved with a rigid prototype balloon (Scheller B, Speck U, Abramjuk C, Bernhardt U, Böhm M, Nickenig G. Paclitaxel balloon coating—a novel method for prevention and therapy of restenosis. Circulation 2004; 110: 810-814). The application of the same coating composition to more flexible modern balloon catheters resulted in problems, i.e., larger premature loss of the drug.

PRIOR ART: PROTECTION FROM PREMATURE DRUG RELEASE

Premature release of a drug from a balloon is a major problem which has been addressed by a variety of methods. Some of them are mechanical, e.g. the use of protection tubes, sleeves, envelops. Examples are U.S. Pat. No. 5,370,614, U.S. Pat. No. 6,306,166, and U.S. Pat. No. 6,616,650 disclosing various protective sheaths which are retracted before the balloon is inflated, or U.S. Pat. No. 6,419,692 proposing a cover which bursts during balloon expansion. A different approach is taken in U.S. Pat. No. 5,893,840 disclosing structured balloon membranes with tiny cavities, WO 94/23787 with roughened balloon membranes to enhance the adherence of coating, or more recently U.S. Pat. No. 7,108,684 proposing a pouch which protects the drug-containing layer on the balloon and WO 2009/066330 disclosing methods placing the drug selectively under the folds of a folded balloon. Although efficacious these methods have the disadvantage of increasing the complexity and cost of production or make handling of the devices more difficult or add to the diameter of the devices (which must be kept as small as possible to facilitate passage through stenotic lesions). In some embodiments the protective membranes or perforated membranes prevent a homogeneous transfer of the drug to the tissue or even put the patient at risk.

Other approaches use either physical or chemical methods to control the release of drugs from a balloon surface, e.g. U.S. Pat. No. 5,304,121 describes a hydrogel which releases the drug only after exposure to a triggering agent; U.S. Pat. No. 5,199,951 relies on thermal activation; according to U.S. Pat. No. 7,445,792 a lipophilic 'hydration inhibitor' protects water-soluble drugs from premature release; and according to U.S. Pat. No. 5,370,614 a viscous matrix protects the drug from premature release, however the viscous matrix must be protected by a sheath during the passage to the stenotic vessel segment. None of the methods has been tested in practice and proven to fulfill the requirements for fast, reliable and complete drug transfer to the target tissue.

Numerous methods of sustained drug release are known and successfully used in practice but are not applicable to medical devices which are in contact with the target tissue for only a few seconds or minutes. Sustained drug release is usually achieved by embedding the drug in a polymer which restricts the diffusion rate to the surface and in this way controls the transfer into the adjacent tissue.

Therefore, a need remains for a method or formulation which protects the coating from premature losses during production, handling, and on the way to the lesion and still allows the immediate and complete release of the active ingredient at a location and point in time determined by the user.

An advantageous way to control adherence and release of a drug from a medical device, e.g., an angioplasty balloon, is the selection of a suitable formulation and coating, which do not require mechanical protection, or additional physical or chemical interaction with the coating except the usual operation of the device e.g. inflation of a folded balloon to induce the release of the drug. Although desirable and frequently tried, the conflicting objectives of perfect adherence before use and immediate release at the site of action make it a difficult task. A large variety of patent applications vaguely disclose measures, compositions and devices to solve this problem either by the selection of drugs, the choice of specific coating processes or formulations containing various additives. Long lists of compounds have been copied from textbooks of chemistry, pharmacology, or pharmacy but even with extensive experimentation disclosures are not sufficiently clear to allow a person familiar with the subject and skilled in the art to come to a satisfactory solution without an inventive step. Examples of prior art are US 2008/0118544 reciting an excessive number of substances and substance classes or U.S. Pat. No. 7,445,795 which discloses the use of 'hydration inhibitors' not applicable to the preferred class of very lipophilic drugs which require 'hydration enhancers' as e.g. disclosed in WO 2004/028582. Although the hydrophilic additives (which may be regarded as 'hydration enhancer') work quite well on certain balloon membranes (Scheller B, Speck U, Abramjuk C, Bernhardt U, Böhm M, Nickenig G. Paclitaxel balloon coating—a novel method for prevention and therapy of restenosis. Circulation 2004; 110: 810-814) the adherence of Limus drugs to various modern PTA or PTCA balloons is either too weak or too tight resulting in premature loss of a major proportion of the drug or incomplete release at the target site.

PRIOR ART: ANTIOXIDANTS

In theory, an antioxidant addresses an almost universal feature of diseased tissue, namely the 'reactive oxygen species', and should have widespread medical applications.

In practice, only very few controlled clinical trials have shown beneficial effects of antioxidants (Suzuki K. Antioxidants for therapeutic use: Why are only a few drugs in clinical use? Adv Drug DelivRev 2009; 61:287-289). Antioxidants are mentioned as potentially useful drugs for the treatment of focal vascular disease such as stenosis, restenosis, atherosclerotic plaques, and vulnerable plaques and the like in US 2009/0136560 with no additive, in U.S. Pat. No. 5,571,523 as agents inducing apoptosis in vascular smooth muscle cells, in WO 2004/022124 either as active drugs or as 'hydration inhibitors'. In US 2008/0241215 probucol, a drug approved for the treatment of hyperlipidemia, a known risk factor for atherosclerosis, is proposed as the active ingredient in stent coating, either alone or combined with rapamycin or another anti-restenotic agent in a slow-release formulation. None of the above-mentioned documents contains data encouraging the use as additives to a lipophilic drug to delay the release rate of the drug and no specific compositions are disclosed which address the above-mentioned problems of adhesion of a drug before the target lesion is reached and immediate release when required.

Small proportions of antioxidants are commonly used to protect drugs or nutrients from decomposition by oxygen or oxidation, an application which has also been proposed for drugs coated on implantable medical devices such as stents (US 2007/0020380, US 2009/0246253) or balloon catheters (US 2009/0246252, especially paragraph [105]). However, antioxidants are commonly used in proportions of less than 1% by weight in relation to 100% by weight of the drug. Normally it is intended to use as less antioxidant as possible, i.e. less than 0.1% by weight in relation to 100% by weight of the drug (Voigt R. Lehrbuch der pharmazeutischen Technologie. 5. Edition, Verlag Chemie, Weinheim—Deer-field Beach, Fla.—Basel, 1984).

PRESENT INVENTION

The problem underlying the present invention was the provision of a medical device with an improved adherence of the drug without negative effect on the release of the drug at the target site.

The problem was solved by a medical device according to claim 1. In other words, the problem was solved by a medical device carrying at least on a portion of its surface a Limus drug or Limus drug preparation and butylated hydroxytoluene at a ratio of 3-100% by weight of butylated hydroxytoluene in relation to 100% by weight of the Limus drug. Preferred embodiments are disclosed in the dependant claims.

During testing of a large variety of coating methods, additives and drug combinations the surprising discovery was made that butylated hydroxytoluene, a well known antioxidant added to a representative of the Limus drugs, an even more lipophilic and less water soluble class of compounds in a defined mass ratio significantly increases the adherence of the drug to a state of the art balloon membrane during handling and on the way to the target lesion even if the target lesion is located far away from the site where the device first enters a blood filled introductory sheath, guiding catheter or vessel containing rapidly flowing blood. Thus, butylated hydroxytoluene in an amount of 3-100% by weight was used as an adherence improver for Limus drugs coated on a medical device.

Preferred active drugs are immunosuppressants belonging to the class of substances binding to the mammalian target of rapamycin (mTOR), i.e. mTOR inhibitors such as sirolimus, everolimus, zotarolimus, biolimus, temsirolimus, most preferred is sirolimus referred to as Limus drugs.

Preferred additive to these active drugs is butylated hydroxytoluene. Probucol is not a preferred additive.

At the dose density used the chosen antioxidant does not display relevant therapeutic or prophylactic effects in respect of the disease which is treated by the coated medical device nor is the relative amount of the antioxidant chosen to protect the drug from oxidative decomposition. The dose density and the mass relation of the antioxidant to the drug are solely optimized in respect of adherence of the drug to and release from the medical device surface. The antioxidant dose on the medical device is too low to provide the desired pharmacological effect, i.e. it is ineffective on its own. The antioxidant on the medical device is not required to protect the active drug (e.g., the antiproliferative or immunosuppressive drug) from oxidative decomposition during production, sterilization and storage; at least it is not required at the dose or concentration applied according to this invention. 'Not required' means that the active drug is stable enough without the antioxidant or at an antioxidant dose or dose density or ratio to the active drug below the dose according to the present invention. 'Sufficient stability' means that less than 5% of the active drug is lost due to oxidative decomposition between the coating of the device and the use in patients one year after production if stored at ambient temperature (=drug or drug preparation stable against oxidative decomposition).

The dose of the antioxidant on the surface of a medical device may be defined in respect of the therapeutic drug. Preferred relationships (weight/weight) are 3-100% antioxidant of the weight of the drug. For example, if the dose density of the drug is 5 µg/mm$^2$ device surface, the amount of antioxidant is 0.15-5.0 µg/mm$^2$. Higher proportions of the antioxidant may be selected if either the drug is applied at a dose below 3 µg/mm$^2$ device surface or the adherence of the drug to the device surface is further improved. The antioxidant load of the device may preferably reach 10 μg/mm². A higher load is possible. Other preferred ranges for the relationship of antioxidant to drug on a weight/weight basis are 5%-100%, more preferred more than 5% up to 100%, more preferred 10-100%, and even more preferred 20-100% in relation to 100% of the drug. Most preferred are 50-100% in relation to 100% of the drug. Especially the range of more than 5-100% on a weight/weight basis enhances the adherence significantly. More than 5% means that 5.00% by weight are excluded but each higher value up to 100% is included. The relationship may also be defined in respect of moles: in a preferred embodiment the antioxidant is present from 10 mole % relative to the drug to 500 mole %, more preferred is 50 mole % to 500 mol %. Higher amounts of the antioxidant may be useful; they are only excluded if they display on their own significant pharmacological prophylactic or therapeutic effects in respect of the disease to be treated.

Polymer-free coating compositions are preferred. It is a special advantage of the present compositions that they do not require the use of polymers to prevent premature release of the drug.

Usually, drugs and mixtures of drugs with additives are coated on medical devices as liquid formulations in volatile solvents. The choice of solvent is important for the structure of the coating in dry state and the adherence and release of the drug from the surface. Preferred organic solvents are acetone, and various alcohols such as methanol, ethanol, and isopropyl alcohol. Usually, 1 to 30% (volume/volume) water is added. The drug or drugs and the antioxidant may be applied at the same time dissolved in the same solvent or mixture of solvents. Alternatively, they may be separately dissolved in the same or different solvents and sequentially applied. In a preferred embodiment, the medical device has been coated with a Limus drug and butylated hydroxytoluene both together or each separately dissolved in acetone or a mixture of solvents containing more than 25% (v/v) acetone. Another preferred embodiment is based on a medical device which has been coated with a Limus drug and butylated hydroxytoluene both together or each separately dissolved in isopropanol or a mixture of solvents containing more than 25% (v/v) isopropanol. Coating with dry particles such as micro- or nanoparticles, crystals, capsules etc. or particles suspended in a liquid preparation is possible. Coating with particles may be facilitated by a roughened or sticky surface of the medical device.

A variety of coating procedures providing more or less uniform layers on medical devices are known from the literature and are disclosed in patent applications. These include simple dipping, spraying, and methods providing precise doses and homogeneous distributions (e.g., WO 2009/018816). Coating may be applied stepwise, either as multiple layers of the same composition or as layers with different compositions e.g. the drug first and the antioxidant second or in the opposite order. All these methods may be applied to the formulations of the current invention. Furthermore, coated medical devices may be dried under different conditions such as temperature, air flow, gas composition, and pressure at different stages of the production process. They may be stored in water-vapor-tight seals with a separately packed water-absorbing agent within the seal.

Preferred medical devices are balloon catheters, e.g., catheters for angioplasty or coronary angioplasty. Preferred are balloon catheters for short-lasting use during an interventional image guided therapy. Short lasting use means that the device is not implanted but eliminated from the body when the procedure is finished, usually within less than 10 minutes, but never later than a few, preferably 5, hours after the end of the procedure. Catheters may contain balloon membranes made from various polymers and copolymers, polyamides (nylon 12, pebax), polyethylenes, polyurethanes, various polyvinyls and the like. Independently of the type of material, the adherence and release properties of drugs are improved by the addition of butylated hydroxytoluene.

The medical device carries the Limus drug or the Limus drug preparation and the butylated hydroxytoluene at least on a portion of its surface which is aimed at coming into close contact with the tissue to be treated, e.g., a balloon at the distal portion of a catheter shaft. This means that at least 5%, preferably more than 50%, most preferably more than 90% of the surface is coated. Preferably, the coating is present at least on the surface of the device where it has the widest diameter. If less than 100% of the device's surface is coated, preferably the parts starting with the lowest device diameter are omitted. However, parts such as holds/handles or shanks are omitted per se. A balloon catheter, which is a preferred medical device, has a central cylindrical part and two opposite conical ends. If less than 100% of the balloon catheter's surface is coated, it is preferred that the cylindrical part is coated and that at least parts of or the complete conical ends remain uncoated.

Below, the invention is described by means of Examples.

EXAMPLE 1

Butylated Hydroxytoluene (BHT) Added to Sirolimus Coated on Balloon Catheters; Sirolimus Dose Density Up to 7 μg/Mm² Balloon Surface Balloons for percutaneous transluminal coronary angioplasty (Cordis Fire Star catheters, Cordis Corp., USA) were coated either with sirolimus alone or combined with different amounts of BHT. Coated balloons were tested in respect of sirolimus loss during the passage through a hemostatic valve, Medtronic Launcher JL 3.5 6F guiding catheter, and one minute in stirred blood (37° C.). When admixed at sufficient concentration to the coating solution BHT improved the adhesion of sirolimus without affecting the release of the drug (sirolimus) during balloon expansion in the coronary arteries of swine (97% of dose released within 1 min without and with BHT). At the dose level applied, BHT does not significantly increase the stability of sirolimus on a balloon catheter and without sirolimus, it does not inhibit neointimal proliferation.

| Hydrophilic balloon surface | Solvent | BHT, % weight of sirolimus | Loss on the way to the lesion, % |
|---|---|---|---|
| yes | Acetone/ | no | 78 ± 5 |
| yes | methanol/ | 1% BHT | 76 ± 3 |
| yes | water | 5% BHT | 40 ± 13 |
| yes |  | 24% BHT | 13 ± 38 |
| no | Acetone/ | no | 49 ± 3 |
| no | methanol/ | 1% BHT | 49 ± 4 |
| no | water | 5% BHT | 33 ± 5 |
| no |  | 24% BHT | 30 ± 7 |
| yes | Isopropanol/ | no | 22 ± 7 |
| yes | water, 3.4 + 1 | 1% BHT | 21 ± 1 |
| yes | (v + v) | 5% BHT | 2 ± 5 |

The invention claimed is:

1. An angioplasty balloon catheter for short lasting use during an interventional image guided procedure carrying at least on a portion of its surface a Limus drug or Limus drug preparation and butylated hydroxytoluene at a ratio of 10-100% by weight of butylated hydroxytoluene in relation to 100% by weight of the Limus drug wherein said Limus drug or Limus drug preparation has an improved adherence to the angioplasty balloon catheter without negative impact on the Limus drug or Limus drug preparation release, and wherein the Limus drug is an mTOR inhibitor selected from sirolimus, everolimus, zotarolimus, biolimus and temsirolimus.

2. The angioplasty balloon catheter according to claim 1 wherein the butylated hydroxytoluene is contained at a ratio of 20-100% by weight in relation to 100% by weight of the Limus drug.

3. The angioplasty balloon catheter according to claim 1 wherein the Limus drug is sirolimus.

4. The angioplasty balloon catheter according to claim 1 which has been coated with a Limus drug and butylated hydroxytoluene both together or each separately dissolved in acetone or a mixture of solvents containing more than 25% (v/v) acetone.

5. The angioplasty balloon catheter according to claim 1 which has been coated with a Limus drug and butylated hydroxytoluene both together or each separately dissolved in isopropanol or a mixture of solvents containing more than 25% (v/v) isopropanol.

6. The angioplasty balloon catheter according to claim 2 which has been coated with a Limus drug and butylated hydroxytoluene both together or each separately dissolved in acetone or a mixture of solvents containing more than 25% (v/v) acetone.

7. The angioplasty balloon catheter according to claim 3 which has been coated with a Limus drug and butylated hydroxytoluene both together or each separately dissolved in acetone or a mixture of solvents containing more than 25% (v/v) acetone.

8. The angioplasty balloon catheter according to claim 2 which has been coated with a Limus drug and butylated hydroxytoluene both together or each separately dissolved in isopropanol or a mixture of solvents containing more than 25% (v/v) isopropanol.

9. The angioplasty balloon catheter according to claim 3 which has been coated with a Limus drug and butylated hydroxytoluene both together or each separately dissolved in isopropanol or a mixture of solvents containing more than 25% (v/v) isopropanol.

* * * * *

UNITED STATES PATENT AND TRADEMARK OFFICE
CERTIFICATE OF CORRECTION

PATENT NO. : 9,629,942 B2  
APPLICATION NO. : 13/641490  
DATED : April 25, 2017  
INVENTOR(S) : Ulrich Speck Page 1 of 1

It is certified that error appears in the above-identified patent and that said Letters Patent is hereby corrected as shown below:

On the Title Page

(73) Assignee: "Innora GmbH, Berlin (DE); Cordin Corporation, Warren, NJ (US)" should be
-- Innora GmbH, Berlin (DE); Cordis Corporation, Warren, NJ (US) --

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*